US009745568B2

(12) United States Patent
Fozdar

(10) Patent No.: US 9,745,568 B2
(45) Date of Patent: Aug. 29, 2017

(54) OPTOFLUIDIC MICRODEVICE FOR IN-VITRO LASER SURGERY AND TRANSFECTION INVOLVING CELLS AND MICROORGANISMS

(71) Applicant: David Fozdar, Edmond, OK (US)

(72) Inventor: David Fozdar, Edmond, OK (US)

(73) Assignee: David Fozdar, Edmond, OK (US)

( * ) Notice: Subject to any disclaimer, the term of this patent is extended or adjusted under 35 U.S.C. 154(b) by 15 days.

(21) Appl. No.: 14/256,853

(22) Filed: Apr. 18, 2014

(65) Prior Publication Data

US 2014/0329325 A1   Nov. 6, 2014

Related U.S. Application Data

(60) Provisional application No. 61/813,622, filed on Apr. 18, 2013.

(51) Int. Cl.
  *C12N 13/00*  (2006.01)
  *C12N 15/89*  (2006.01)
  *C12M 1/42*  (2006.01)

(52) U.S. Cl.
  CPC ............. *C12N 13/00* (2013.01); *C12M 35/02* (2013.01); *C12N 15/89* (2013.01)

(58) Field of Classification Search
  CPC ... B01L 3/5085; B01L 3/50857; C12M 35/02; C12N 15/89; C12N 13/00
  See application file for complete search history.

(56) References Cited

U.S. PATENT DOCUMENTS

| 2003/0059936 | A1* | 3/2003 | Baumann | ............... | C12M 35/02 |
| | | | | | 435/325 |
| 2007/0048857 | A1* | 3/2007 | Ito | ...................... | B01L 3/50857 |
| | | | | | 435/283.1 |

(Continued)

FOREIGN PATENT DOCUMENTS

JP     2000023657 A2 *  1/2000  .............. C12M 1/00

OTHER PUBLICATIONS

Valero A, Post JN, van Nieuwkasteele JW, ter Braak PM, Kruijer W, van den Berg A. Gene transfer and protein dynamics in stem cells using single cell electroporation in a microfluidic device. Lab on a Chip; 8(1) pp. 62-67 (2008).*

(Continued)

*Primary Examiner* — Sean E Conley
*Assistant Examiner* — Benjamin R Whatley
(74) *Attorney, Agent, or Firm* — Crowe & Dunlevy, P.C.

(57) ABSTRACT

A device for use in laser optical transfection of biological targets including an optofluidic microdevice and a piece of optical glass. The optofluidic microdevice has a central vertical outlet and a microchannel network that includes a plurality of entrapping channels with narrowings. The microchannel network is fused with the optical glass. In one aspect the device is used with a petri dish having an optical window. In another aspect the device is used with a well plate having a plurality of wells and associated optical windows. In a third aspect the device is used with a barrier. Each of the aspects forms a peripheral space around the optofluidic microdevice capable of retaining a live culture of biological targets and material that is desired to be injected into those biological targets. Polymer tubing is inserted into the central vertical outlet which connects the device to an external pump. The external pump provides an inward suction force which draws the biological targets from the peripheral space into the microchannel network. The biological targets are then captured at the openings or within the narrowings in the entrapping channels of the microchannel network where they can be transfected by laser light emitting from a laser through the optical glass.

12 Claims, 10 Drawing Sheets

(56) References Cited

U.S. PATENT DOCUMENTS

2009/0215104 A1* 8/2009 Taboas .................. C12M 23/16
                                                           435/29
2012/0034622 A1* 2/2012 Ignatius .................. B82Y 5/00
                                                           435/7.2

OTHER PUBLICATIONS

Py C, Martina M, Diaz-Quijada GAa, Luk CC, Martinez D, Denhoff MW, Charrier A, Comas T, Monette R, Krantis A, Syed NI, Mealing GAR. From understanding cellular function to novel drug discovery: the role of planar patch-clamp array chip technology. Frontiers in Pharmacology; 2: pp. 1-16 (2011).*

Fozdar, DY, Lee, JY, Schmidt CE, Chen S. Selective axonal growth of embryonic hippocampal neurons according to topographic features of various sizes and shapes. International Journal of Nanomedicine; 6: pp. 45-57 (2010).*

Marchington RF, Arita Y, Tsampoula X, Gunn-Moore FJ, Dholakia K. Optical injection of mammalian cells using a microfluidic platform. Biomedical optical express. 1(2): pp. 527-536 (2010).*

Arakawa T, Noguchi M, Sumitomo K, Yamaguchi Y, Shoji S. High-throughput single-cell manipulation system for a large number of target cells. Biomicrofluidics; 5: pp. 1-11 (2011).*

Kobel S, Valero A, Latt J, Renaud P, Lutolf M. Optimization of microfluidic single cell trapping for long term on chip culture. Lab on a Chip; 10: pp. 857-863 (2010).*

* cited by examiner

OPTOFLUIDIC MICRODEVICE FOR IN-VITRO LASER SURGERY AND TRANSFECTION INVOLVING CELLS AND MICROORGANISMS

PRIORITY CLAIM

The application claims the benefit of U.S. Provisional Application No. 61/813,622 filed on Apr. 18, 2013.

FIELD OF THE INVENTION

The invention generally related to the field of optofluidic injection by transfection.

BACKGROUND OF THE INVENTION

The general process of incorporating or injecting biomaterials into animal and plant cells or other microorganisms is commonly referred to as transfection. There are several known modes or methods of transfection, often referred to as "delivery" or "biodelivery" methods. Laser optoinjection (also called optoporation or photoporation) is a laser-mediated biodelivery method of transfection wherein biomolecules and other biomaterials (e.g., recombinant DNA, RNA, proteins, and nanoparticles) are incorporated into microbiological organisms (referred to as biological targets) through the outer bi-lipid protecting membrane of cells or other biological targets. Optoinjection can also include the injection of biomolecules through the nuclear membrane of animal and plant cells and eukaryotic microorganisms.

In laser optoinjection transfection, laser light is focused onto a protective barrier (such as a bi-lipid membrane) of a biological target, which causes a localized increase in the barrier's permeability. The localized increase in permeability at the focal point of the laser light allows for the diffusion (or other form of mass transport) of materials into the biological target. Such techniques are desirable to injecting materials into the biological target where the materials cannot otherwise penetrate the protecting barrier of the target. The increase in permeability is only temporary and, in most cases, decreases back to normal in a relatively short span of time. Laser optoinjection is classified as a physical delivery method since transfection (injection) is mediated through the direct structural disruption in a protecting barrier by the laser.

To achieve transfection using laser optoinjection, the laser light must be focused onto the membrane of the biological target with an oil-immersion objective lens that has a high numerical aperture (and thereby a short focal length). Due to the high numerical aperture and associated very short focal length of an oil-immersion lens, the biological target to be irradiated and injected with the laser must be stably positioned within approximately 200 micrometers (±100 micrometers) of the objective. The stable positioning constraints involved in laser optoinjection presents a huge challenge in transfection of biological targets, and is, thus, a major reason why a device for stabilization of the target is necessary for successful commercialization and use of laser optoinjection. The prior art, however, does not disclose adequate techniques or devices for the required stabilization of biological targets.

The inability to transfect biological entities that do not stick to culture surfaces via laser-mediated biodelivery (optoinjection) with limited interference is a major hindrance of the technique(s). Biological entities/targets (cells or other microorganisms) that do not adhere to surfaces are non-adherent. A vast array of non-adherent entities have potential as transfection targets in the modern biotechnology industry/space. The laser optoinjection technique also suffers from extremely low throughput since no robust platform exists to automate the transfection process. Automation would increase injection rates and enable laser-mediated transfection at a large scale. Other significant challenges facing current laser optoinjection methods include difficulties in re-focusing the laser on each biological target, which requires high throughput or the injection of targets that are not closely spaced (i.e., tightly packed together) thereby causing high injection efficiencies (% of cells transfected relative to the number irradiated by the laser). At present, no platform or method exists to enable the laser optoinjection transfection to overcome the above limitations and maintaining compatiblility with desirable enhancements to laser-mediated transfection including in-situ culture, post-injection monitoring/imaging, and intracellular optical tweezing (e.g., to enhance nuclear transfection in eukaryotic entities).

SUMMARY OF THE INVENTION

In the presently preferred embodiment a device for use in optical transfection of biological targets includes an optofluidic microdevice and a piece of optical glass. The optofluidic microdevice has a central vertical outlet and a microchannel network that includes a plurality of entrapping channels. The microchannel network is fused with the optical glass.

The preferred embodiment can be configured to be used in at least three different preferred formats. In the first preferred format, the device is used with a petri dish having an optical window. In the second preferred format, the device is used with a well plate having a plurality of wells and associated optical windows. In the third preferred format, the device is used with a barrier. Each of the formats forms a peripheral space around the optofluidic microdevice capable of retaining a live culture of biological targets and material that is desired to be injected into those biological targets.

In all preferred formats, polymer tubing is inserted into the central vertical outlet which connects the device to an external pump. The external pump provides an inward suction force which draws the biological targets from the peripheral space into the microchannel network. The biological targets are then captured within narrowings in the entrapping channels of the microchannel network where they can be transfected by laser light emitting from a laser through the optical glass.

DETAILED DESCRIPTION

Figure 4A:
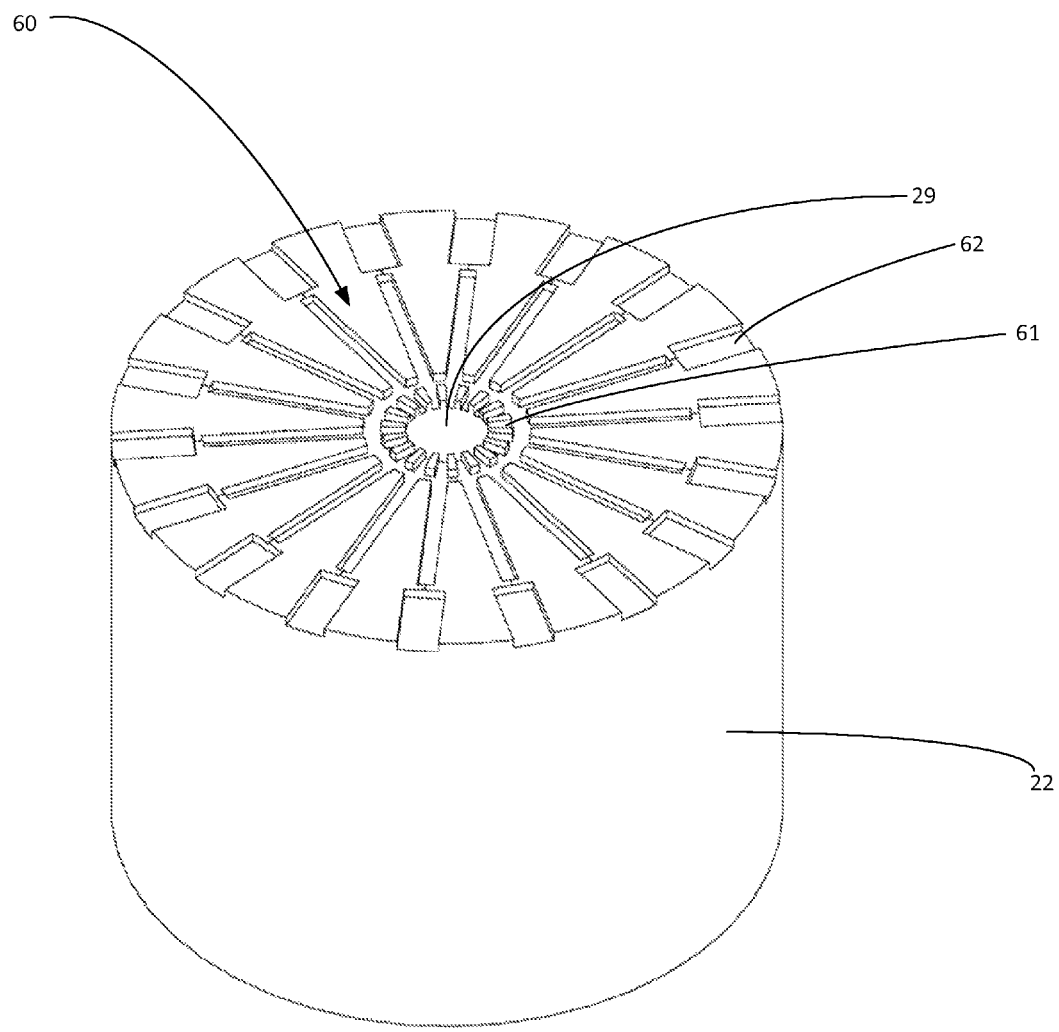
FIG. 4A is a perspective view of an optofluidic microdevice, depicting the layout and dimensions of a microchannel network.
Figure 4B:
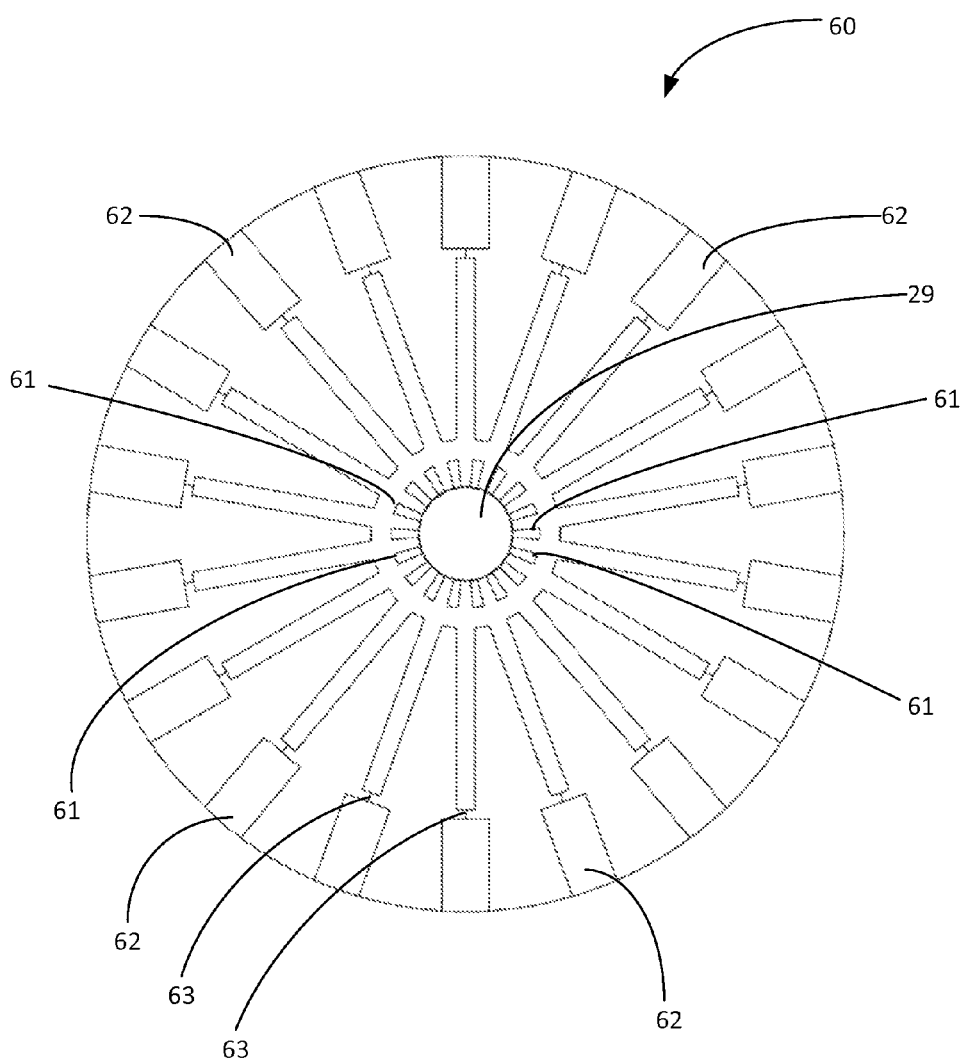
FIG. 4B is a bottom view of an optofluidic microdevice, depicting the layout and dimensions of a microchannel network.
Figure 5A:
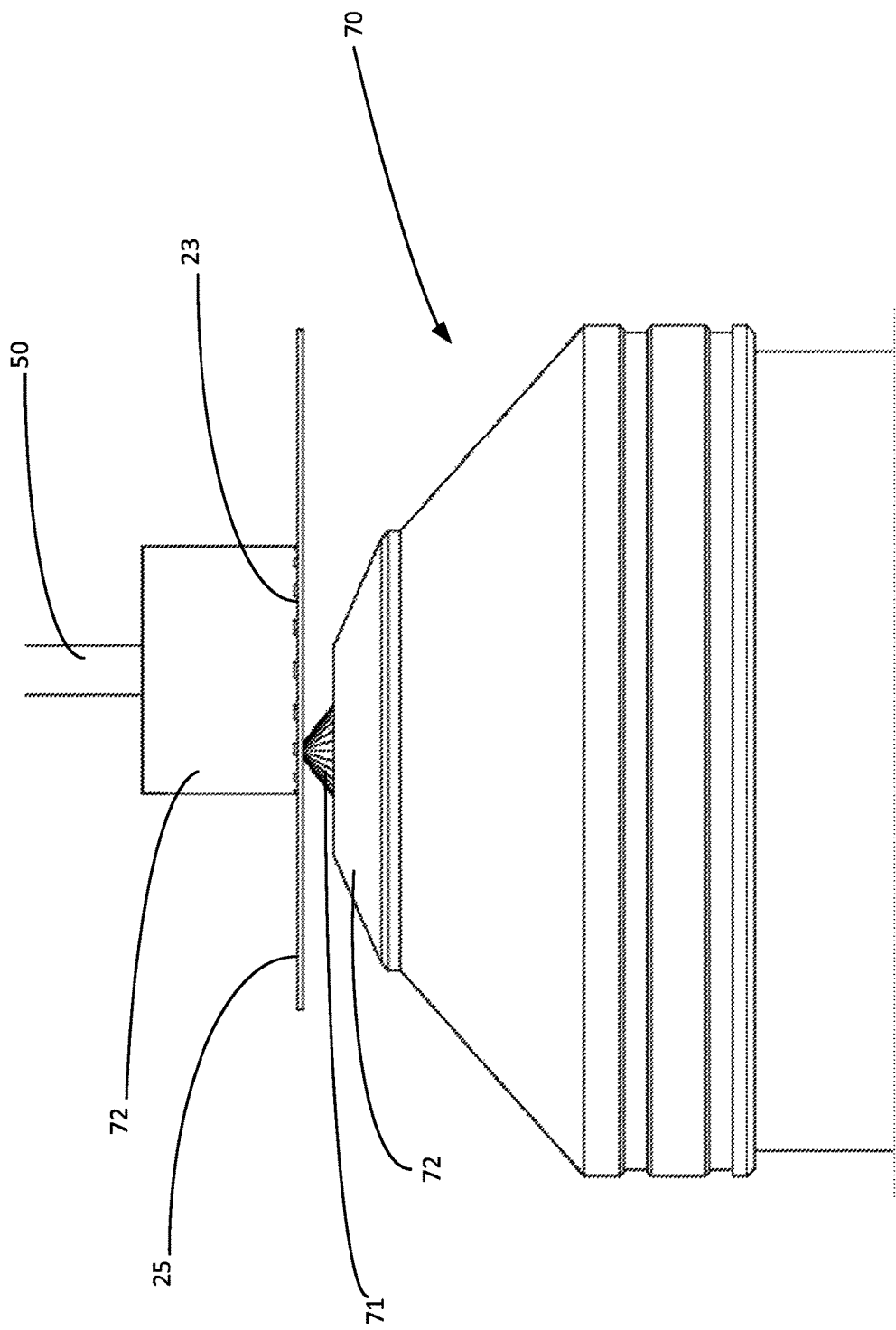
FIG. 5A is a side view depicting laser light being focused by a high numerical aperture objective into an optofluidic microdevice.
Figure 5B:
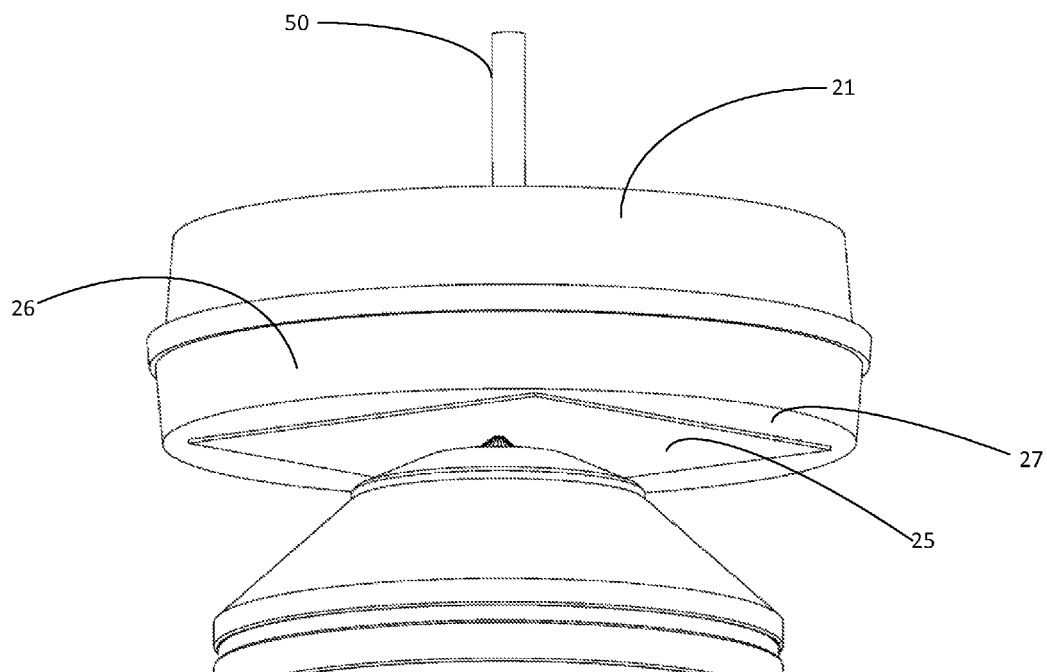
FIG. 5B is a perspective view of an optofluidic microdevice during use, depicting tubing connecting the inlet to the pump, which provides the pulling suction that entraps cells or microorganisms at or within the entrapping channels.

A device for use in optical transfection is further described herein, and includes an optofluidic microdevice 22 and a piece of optical glass 25. The optofluidic microdevice 22 includes a microchannel network 60 and a central vertical outlet 29. Preferably, the optofluidic microdevice 22 is constructed from polydimethysiloxane (PDMS), a clear soft silicone elastomer, or any other translucent (to visible light) biocompatible material capable of forming a leak proof seal with optical glass. The microchannel network 60 includes an array of entrapping channels 62. In the preferred embodiment, the entrapping channels 62 have a rectangular cross-section with narrowings 63 that have a height and width on the order of 1/10 to slightly less than the diameter of the cells to be trapped Inner support pillars 61 ensure that the center of the microchannel network 60, engaging the central outlet hole 29, does not collapse and stick to the optical glass 25 resulting from the low aspect ratio of this portion of the microchannel network 60. It will be understood by those skilled in the art that the dimensions, shape, and layout of the microchannel network can be altered to suit particular applications. The central outlet hole 29 has a diameter that is slightly smaller than the diameter of tubing 50 that is inserted into the central outlet hole 29 during use. FIGS. 4A,B depict the optofluidic microdevice 22, including the layout and shape of the microchannel network 60. The optical glass must sufficiently transmit laser light, be non-toxic/biocompatible, be capable of bonding with the microchannel network 60, and must have a thickness compatible with focusing requirements of a high-numerical aperture focusing lens. In the preferred embodiment, the thickness of the optical glass 25 is approximately 180 micrometers. It will be understood that the wavelength of the laser to be used in the optoinjection or dissection procedure is the primary factor dictating the type of optical glass 25 which must be used in connection with the optofluidic microdevice 22.

Figure 2A:
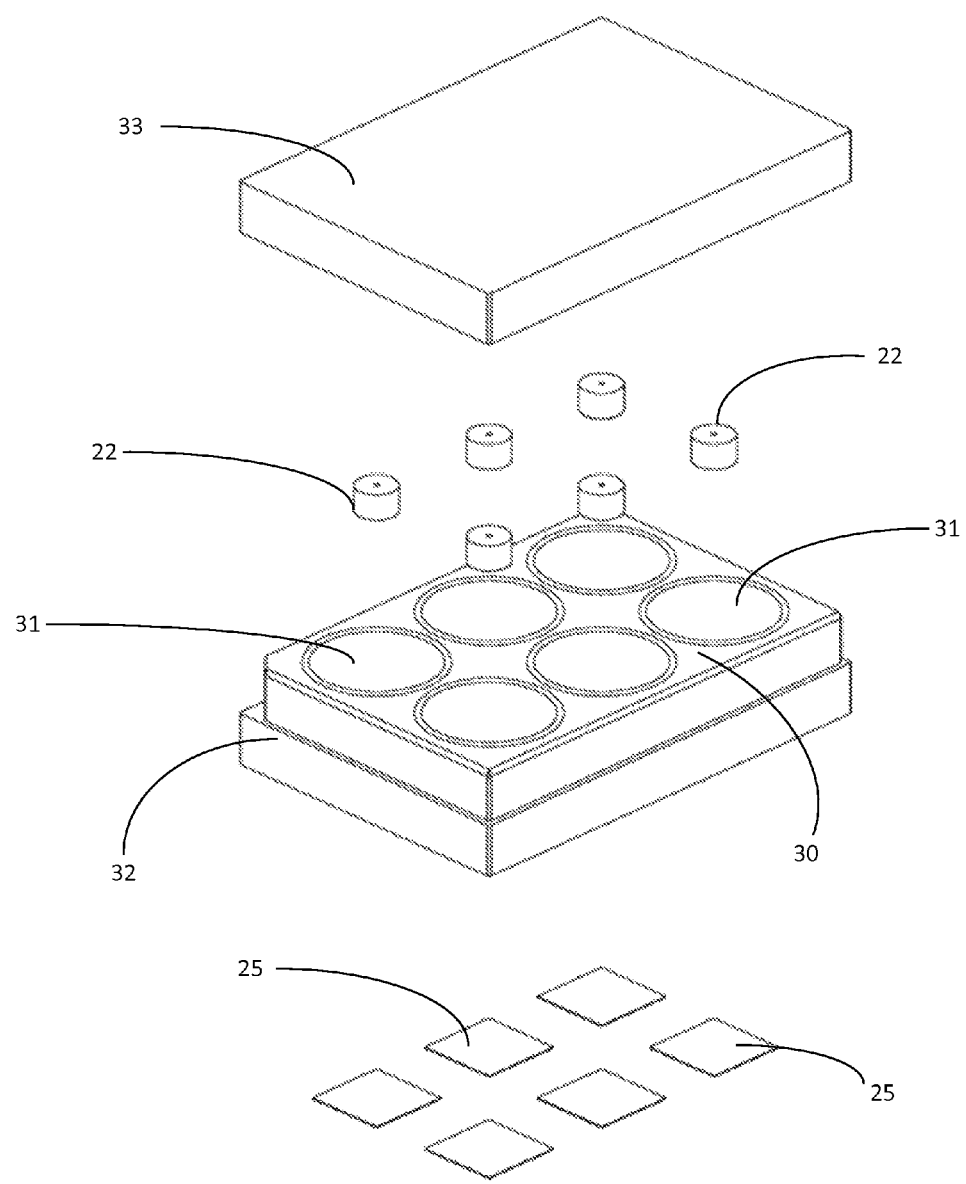
FIG. 2A is an exploded perspective view of an optofluidic microdevice in well plate configuration.
Figure 2B:
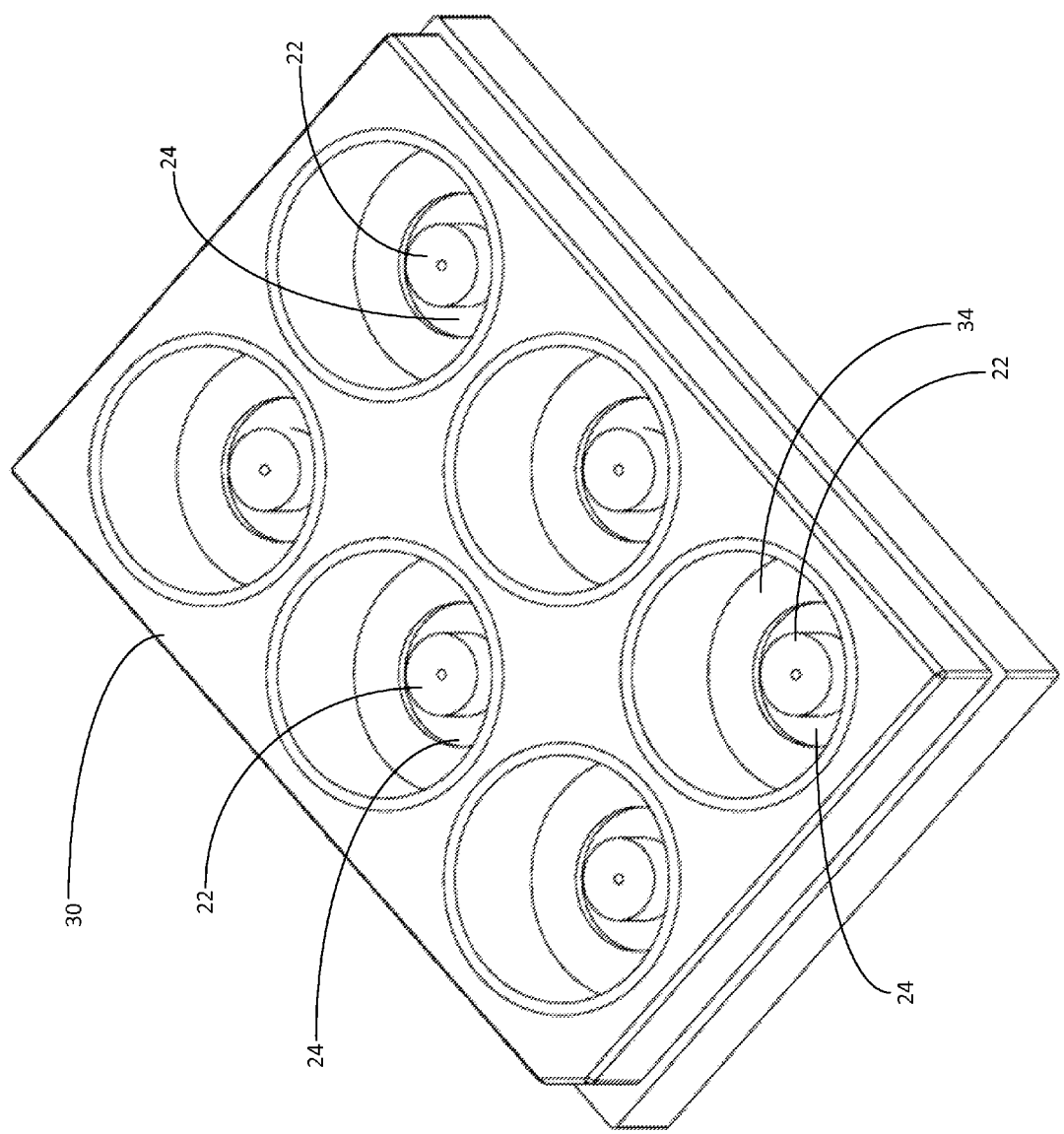
FIG. 2B is a perspective view of an optofluidic microdevice in well plate configuration.
Figure 3:
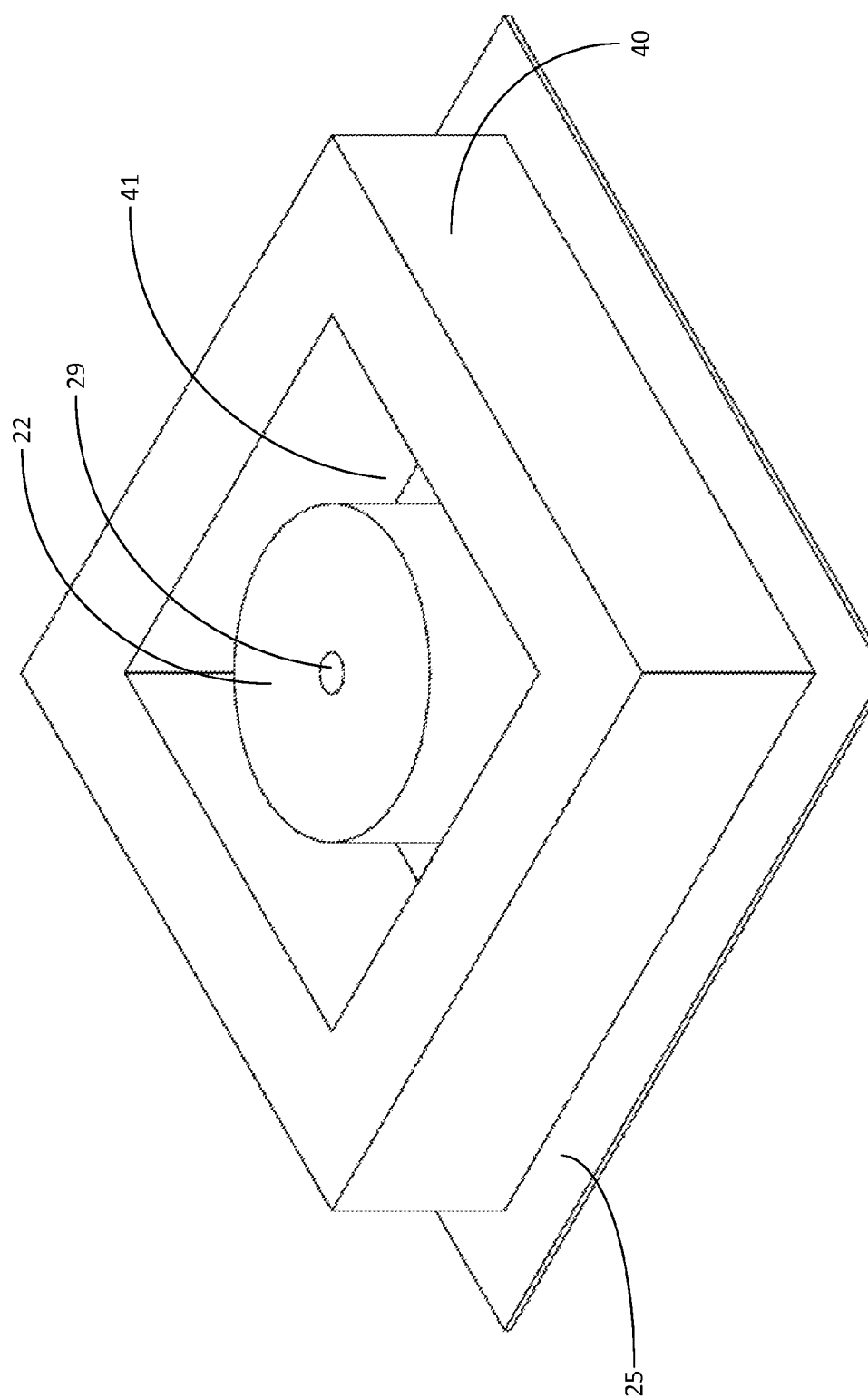
FIG. 3 is an perspective view of the invention in stand-alone configuration.

It will be further understood that the optofluidic microdevice 22 can be used in several preferred formats, including a petri-dish preferred format (FIG. 1A, 1B), a well-plate preferred format (FIG. 2A, 2B), and a stand-alone preferred format (FIG. 3).

Figure 1A:
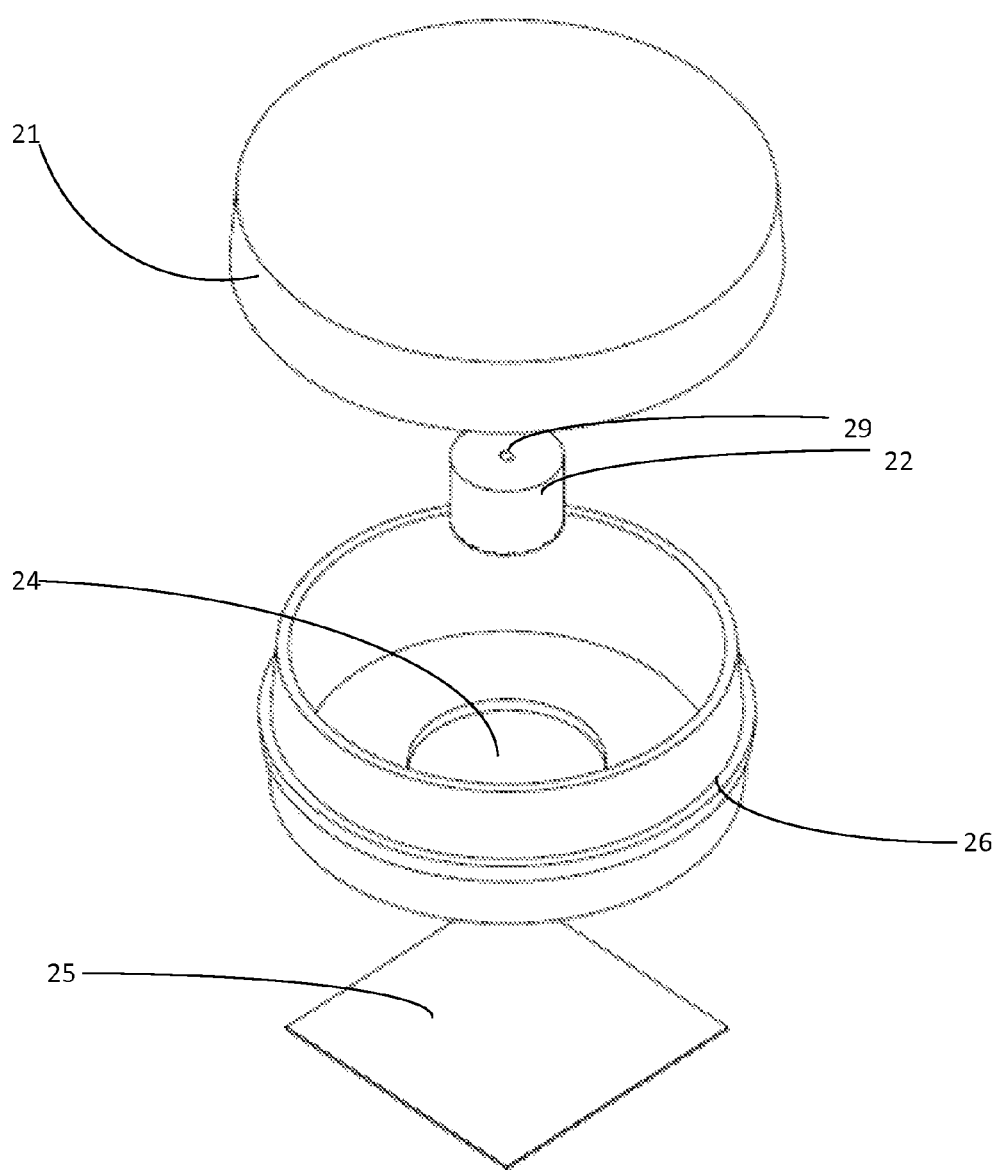
FIG. 1A is an exploded perspective view of an optofluidic microdevice in culture dish configuration.
Figure 1B:
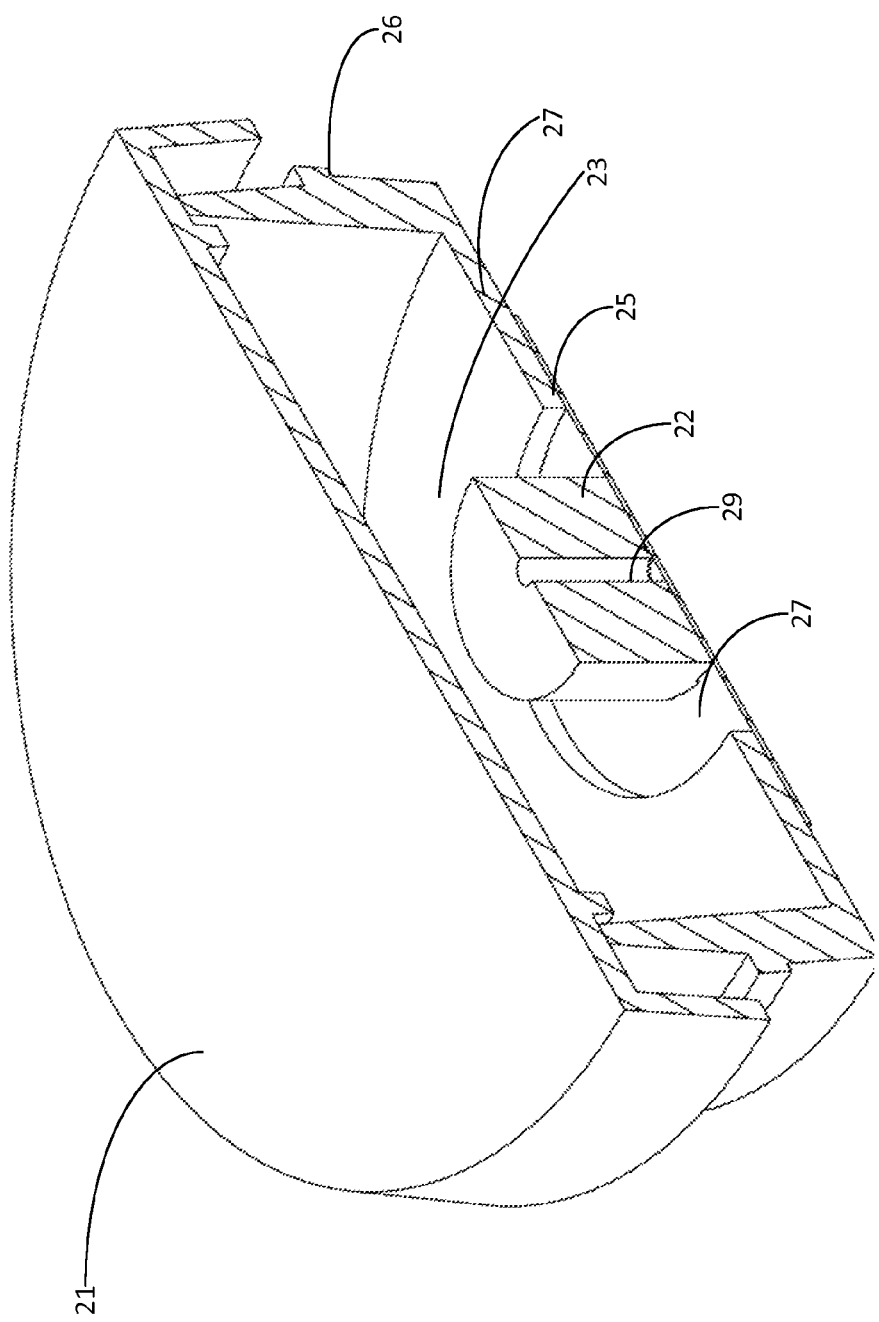
FIG. 1B is a cross-sectional perspective view of an optofluidic microdevice in dish configuration.

In the petri dish format the optofluidic microdevice 22 is bonded to the center of the optical glass 25, as in FIGS. 1A, 1B. The optical glass 25 engages the bottom 27 of petri dish 26 forming a leak-proof seal. An optical window 24 is formed in the bottom 27 of the petri dish 26. In the preferred embodiment, the optical window 24 is a circular hole with a diameter larger than the diameter of the microfluidic microdevice 22. The petri dish includes a lid 21, which fits over the petri dish 26.

Turning to FIGS. 2A, 2B, depicted therein is a well-plate format that includes multiple microdevices 22 each bonded to a piece of optical glass 25. The optical glass pieces 25 are bonded to the bottom 32 of wells 31 in a well-plate 30. In the preferred embodiment, the well-plate 30 is a type of microtiter plate. An optical window 24 is formed in each well 31 in the well-plate 30 similar to the petri-dish preferred format. The well-plate 30 has lid 33 which fits over the bottom 32 of the well-plate 30.

The stand-alone format depicted in FIG. 3 includes a microdevice 22 bonded to optical glass 25. Barrier 40 is bonded to the optical glass 25 to form a leak-proof seal between the optical glass 25 and barrier 40. In the preferred embodiment, the barrier 40 is formed from PDMS or other polymer that can form a tight leak-proof seal so that it can retain a liquid media pipetted around the microdevice. In an alternative embodiment, the barrier 40 is constructed from the same material as the optofluidic microdevice 22.

Tubing 50 is inserted into the central vertical outlet 29 and connected at the other end to an external pump (e.g., syringe pump). For a microchannel network 60 constructed from polydimethylsiloxane (PDMS), elastomeric tubing 50 is inserted directly into the central vertical outlet 29 provided that its outer diameter is slightly larger than that of the central vertical outlet 29. The PDMS stretches and conforms around the larger tubing 50 ensuring the formation of a leak-proof seal between the optofluidic microdevice 22 and the tubing 50. The tubing 50 can also be connected to a needle (not shown), which is inserted into the central vertical outlet 29.

After the optofluidic microdevice 22 is configured into one of the preferred formats, biological targets (cells and microorganisms) and materials desired to be injected (e.g., biomolecule) into those targets are prepared into a liquid culture media and added in the peripheral space 23 (petri dish format), 34 (well plate format) and 41 (stand alone configuration) around the optofluidic microdevice 22. Once the liquid culture media is added, the external pump is switched on creating an inward-directed pressure drop that provides the suction action/forces that pull the biological targets in the peripheral space 23, 34, 41 towards the microchannel network 60 and into entrapping channels 62. Suction forces applied by the external pump pull fluid from the periphery of the optofluidic microdevice 22 inwards through the entrapping channels 62 in microchannel network 60 towards the central vertical outlet 29 of the optofluidic microdevice 22 and out through the tubing 50. Withdrawn fluid is pulled into a syringe or other reservoir connected to the pump as it is providing suction. For the purposes of the preferred embodiments, a syringe pump with a fluid withdrawal feature which draws liquid into the syringe is sufficient to meet the requirements of the embodiments.

Figure 6:
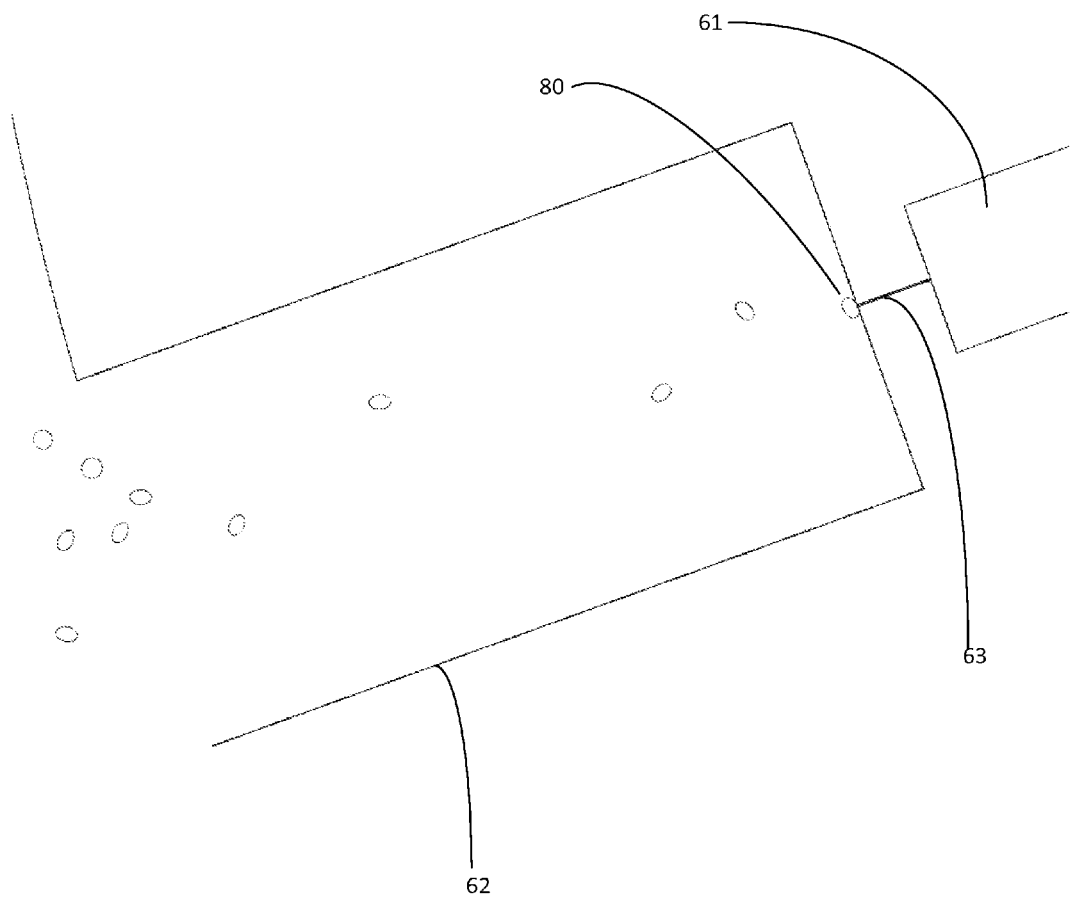
FIG. 6 shows a bottom view of an optofluidic microdevice during use in which a biological target is entrapped at the opening or within the narrowing of an entrapping channel.

Turning to FIG. 6, it will be understood that the suction forces convectively draw the biological target 80 towards a narrowing 63 in one of the entrapping channels 62. It will be understood that the biological target 80 gets captured and held at a particular point within the narrowing 63 where the size of the biological target 80 prevents it from moving further within the narrowing 63. It will be further understood that the narrowing 63 can be tapered such that the optofluidic microdevice 22 can be used in connection with biological targets of various sizes (each of which might be captured at a different point within the narrowing 63). Once a biological target 80 has been captured within an entrapping channel 62 at the narrowing 63, the entrapping channel 62 becomes blocked by the biological target 80 at the narrowing 63 so that other nearby targets are no longer attracted by the particular entrapping channel 62. The biological target 80 remains stationary until the pump providing the suction is switched off. The preferred symmetrical design of the microchannel network 60 ensures that the pressures emanating from each entrapping channel 62 are equivalent.

After a biological target 80 has been captured and is being detained at or within each entrapping channel narrowing 63, the uncaptured cells can be removed by aspirating the culture medium with a pipette and replacing it with fresh culture media that does not contain cells. While removing the remaining suspended cells or microorganisms during the exchange of culture medium, the pump must remain on so that the suction forces can continue to detain the cells at the entrapping channel narrowings 63 by the surface of the optical glass 25.

After a biological target 80 has been captured, and while they are being detained by the entrapping channels 62, they can be irradiated by the laser light. The laser light 71 is focused by high numerical aperture (NA) objective lens 72 so that it travels through the optical glass 25 and has focal point at or within the surface of an individually entrapped biological target 80. The optofluidic microdevice 22 can have translation and rotation so that each entrapped cell or microorganism can be irradiated by the laser. Thus, the laser light 71 can be focused on multiple entrapped biological targets 80 in a one-by-one serial fashion, with the precise location of each entrapped biological target 80 known (position of the entrapping channel narrowings 63 relative to a reference). This enables the automation of laser irradiation to be achievable.

It will be understood that the microchannel network 60 and entrapping channels 62, which include narrowings 63, can be configured so that multiple sizes of biological targets can be captured at the opening (junction) of each narrowing 63 or within each narrowing 63 by adjusting the width of the narrowing 63. If the narrowing 63 has a length and width that is small relative to the target, the target will be captured at the opening of the narrowing 63, blocking the narrowing. If the narrowing 63 is made to be roughly equivalent to the size of the biological target 80, the target will get captured at some point within the narrowing 63. The smaller the narrowing 63, the more difficult it is for the cell to pass through (higher suction pressures required). By configuring the narrowing 63 to gently taper as it approaches the central vertical hole 29, each entrapping channel narrowing 63 will be capable of trapping multiple sizes of targets. In each alternative embodiment, if the cells are capable of entering the narrowings 63, the biological targets 80 will form a single-file line in the narrowing 63, since it is likely not to be completely blocked. Thus, multiple targets 80 can be entrapped in each entrapping channel narrowing 63.

With respect to the above description, many variations in dimensions, materials, shape and form, function and method of operation, assembly and use, will be readily apparent and obvious to one skilled in the art, so accordingly, all variations to the embodiments in the drawings and specifications are intended to be encompassed by the present invention.

Therefore, the foregoing only illustrates the principles of the invention. Since numerous modifications and changes will be made by those skilled in the art, it is not desired to limit the invention to the exact construction and operation shown and described. Accordingly, all suitable modifications and that may be resorted to, indeed, fall within the scope of the invention.

What is claimed is:

1. A device for use in optoinjection transfection, the device comprising:
   a microdevice having a bottom and a center;
   a central vertical outlet formed within the microdevice at its center;
   more than two entrapping channels forming a plurality of entrapping channels positioned on the bottom of the microdevice and engaging the central vertical outlet, wherein each entrapping channel extends radially from the central vertical outlet and is aligned perpendicular to the central axis of the central vertical outlet;
   a piece of optical glass engaging the bottom of the microdevice and forming a seal with the plurality of entrapping channels; and
   a barrier engaging the optical glass, and forming a periphery around the microdevice, wherein the periphery is capable of retaining a solution of biological targets to be transfected;
   wherein the optical glass, plurality of entrapping channels and central vertical outlet are positioned so that a laser beam may pass through the optical glass to separately engage a target in each of the plurality of entrapping channels without passing through the central vertical outlet.

2. The device of claim 1, wherein at least one of the entrapping channel has a narrowing.

3. The device of claim 1, wherein at least one of the entrapping channels has a rectangular cross-section.

4. The device of claim 2, wherein at least one of the entrapping channels has a width that is between 1/10 and slightly less than the diameter of the biological target to be transfected.

5. The device of claim 2, wherein the microdevice further comprises a plurality of inner support pillars configured around the central vertical outlet.

6. The device of claim 2, wherein the barrier is a petri dish having an optical window, wherein the petri dish engages the optical glass.

7. The device of claim 2, wherein the microdevice is manufactured from a silicone elastomer.

8. The device of claim 3, wherein the silicone elastomer is polydimethylsiloxane.

9. The device of claim 1, wherein each of the entrapping channels in the plurality of entrapping channels are equidistant from the central vertical outlet.

10. The microdevice of claim 9, wherein the microdevice is cylindrical and configured to fit within a cylindrically shaped well.

11. The device of claim 10, wherein the plurality of entrapping channels is arranged in a manner such that an equal negative pressure is exerted against a biological target in each of the entrapping channels in the plurality of entrapping channels.

12. A device for use in laser optical transfection, the device comprising:
   a microdevice manufactured from polydimethylsiloxane and having a bottom, a center and plurality of inner support pillars;
   a central vertical outlet formed within the microdevice at its center and surrounded by the plurality of inner support pillars;
   more than two entrapping channels forming a plurality of entrapping channels with narrowings positioned on the bottom of the microdevice, aligned perpendicular to the central axis of the central vertical outlet, extending radially from the central vertical outlet, and engaging the central vertical outlet, wherein at least one of the narrowings has a rectangular cross-section;
   a piece of optical class engaging the bottom of the microdevice and forming a seal with the plurality of entrapping channels and narrowings; and a petri dish having an optical window, engaging the optical glass and forming a periphery around the microdevice, wherein the periphery is capable of retaining a solution of biological targets to be transfected.

* * * * *